US010557235B2

(12) United States Patent
LeBel

(10) Patent No.: US 10,557,235 B2
(45) Date of Patent: Feb. 11, 2020

(54) ULTRASONIC SEMELT DISSOLVING AND SHATTERING SYSTEM

(71) Applicant: Andritz Inc., Glens Falls, NY (US)

(72) Inventor: Mark LeBel, Alpharetta, GA (US)

(73) Assignee: Andritz Inc., Alpharetta, GA (US)

( * ) Notice: Subject to any disclaimer, the term of this patent is extended or adjusted under 35 U.S.C. 154(b) by 48 days.

(21) Appl. No.: 16/040,333

(22) Filed: Jul. 19, 2018

(65) Prior Publication Data

US 2019/0024310 A1   Jan. 24, 2019

Related U.S. Application Data

(60) Provisional application No. 62/535,338, filed on Jul. 21, 2017.

(51) Int. Cl.
| | |
|---|---|
| *D21C 11/12* | (2006.01) |
| *G01N 29/22* | (2006.01) |
| *D21C 11/04* | (2006.01) |

(52) U.S. Cl.
CPC ............ *D21C 11/122* (2013.01); *D21C 11/04* (2013.01); *G01N 29/221* (2013.01)

(58) Field of Classification Search
CPC .................................................. D21C 11/122
See application file for complete search history.

(56) References Cited

U.S. PATENT DOCUMENTS

| | | | | |
|---|---|---|---|---|
| 2,967,758 A | * | 1/1961 | Thorson ............... | D21C 11/122 |
| | | | | 423/204 |
| 4,761,204 A | | 8/1988 | Kohl et al. | |
| 5,413,675 A | | 5/1995 | Ikonomou et al. | |
| 5,976,319 A | | 11/1999 | Paju et al. | |
| 6,228,273 B1 | * | 5/2001 | Hammonds ............... | C02F 1/34 |
| | | | | 210/205 |
| 2008/0087302 A1 | * | 4/2008 | Koskela ..................... | F23J 1/08 |
| | | | | 134/22.11 |
| 2017/0131240 A1 | * | 5/2017 | Aura ...................... | D21C 11/10 |

FOREIGN PATENT DOCUMENTS

| | | |
|---|---|---|
| WO | 2005017001 | 2/2005 |
| WO | 2008046959 | 4/2008 |
| WO | 2010058185 | 5/2010 |
| WO | 2012052617 | 4/2012 |
| WO | 2013071008 | 5/2013 |

OTHER PUBLICATIONS

Taranenko, Shattering Kraft Recovery Boiler Smelt by Steam Jet, 2013, University of Toronto. (Year: 2013).*

(Continued)

*Primary Examiner* — Anthony Calandra
(74) *Attorney, Agent, or Firm* — Robert J. Hornung

(57) ABSTRACT

The problem of runaway smelt explosions due to a sudden influx of smelt into a dissolving tank is mitigated by a system comprising an ultrasonic transducer configured to emit ultrasonic waves toward the dissolving tank at a frequency above 20 kilohertz. A system comprising the ultrasonic transducer may further comprise sensors and a data processor configured to regulate the properties of the ultrasonic waves in response to process conditions affecting the smelt flow.

14 Claims, 2 Drawing Sheets

(56) References Cited

OTHER PUBLICATIONS

Karlsson, Lennart, European Search Report, dated Nov. 6, 2018, pp. 1-7, Munich, Germany.
Markus Bussmann et. al., Experiments on Smelt Shattering and Dissolution, Journal of Science & Technology for Forest Products and Processes: vol. 4, No. 6, Canada.
Hugo Lepage el al., Passive Acoustic Monitoring of Recovery Boiler Dissolving Tank Operation, Proceedings of The Canadian Society for Mechanical Engineering International Congress Jun. 2014, Toronto, Ontario, Canada.

* cited by examiner

ULTRASONIC SEMELT DISSOLVING AND SHATTERING SYSTEM

RELATED APPLICATION

This application claims the benefit of U.S. Provisional Patent Application Ser. No. 62/535,338, filed on Jul. 21, 2017, and entitled "Ultrasonic Smelt Dissolving and Shattering System," the entirely of which is incorporated herein by reference.

BACKGROUND OF THE INVENTION

Technical Field

The present disclosure relates generally to chemical pulping and particularly to recovery boilers and dissolving tanks used in the pulp and paper industry.

Related Art

In the chemical pulping industry, mill operators treat lignocellulosic material with either strong acids or strong bases to disassociate the lignin from the cellulosic fibers. Operators may then separate, wash, and further process the cellulosic fibers into pulp or other pulp-based products. Chemical process examples include: the Kraft process (also known as the "sulfate process"), the sulfite process, the soda pulping process, and the sulfite semi-chemical pulping process.

While the processing chemicals for each type of chemical process may vary, mill operators frequently recover and recycle these process chemicals to operate the mill economically. For example, in the Kraft process, mill operators digest lignocellulosic material (commonly wood chips) in large pressurized vessels with "white liquor" comprising sodium hydroxide (NaOH) and sodium sulfide ($Na_2S$). During the digestion step, the white liquor reacts with lignin and other compounds in the lignocellulosic material and takes on a dark color. Unsurprisingly, this reacted liquor is known as "black liquor." Whereas the white liquor comprises the reactants sodium hydroxide (NaOH) and sodium sulfide ($Na_2S$), the black liquor contains the chemical products sodium carbonate ($Na_2CO_3$) and sodium sulfate ($Na_2SO_4$). While sodium hydroxide (NaOH) and sodium sulfide ($Na_2S$) are generally inexpensive, it is generally cost prohibitive to purchase new solutions of sodium hydroxide (NaOH) and sodium sulfide ($Na_2S$) to maintain production. For this reason, many chemical pulp mills use pyrolytic chemical recovery systems to recycle at least a portion of the produced sodium carbonate ($Na_2CO_3$) and sodium sulfate ($Na_2SO_4$). Converting these products back into the commercially useful chemical reactants, sodium hydroxide (NaOH) and sodium sulfide ($Na_2S$), allows mills to run economically.

New black liquor from a chemical digester is generally dilute and non-combustible. Therefore, to prepare black liquor for pyrolysis, operators generally funnel the black liquor through flash tanks or other evaporation steps to concentrate the solid particles in the black liquor. Operators then heat and inject the concentrated black liquor into a chemical recovery boiler. The recovery boiler evaporates the remaining water from the black liquor droplets and the solid compounds in the black liquor undergo partial pyrolysis. The remaining inorganic compounds fall to the bottom of the furnace and accumulate in a char bed. Some of the carbon and carbon monoxide in the char bed acts as a catalyst to convert most of the sodium sulfate ($Na_2SO_4$) into sodium sulfide ($Na_2S$). The sodium sulfide ($Na_2S$) then exits the recovery boiler with the sodium carbonate ($Na_2CO_3$) as liquid smelt.

This smelt flows through one or more smelt spouts at the bottom of the recovery boiler. Coolant, usually water, may cool the smelt spouts. Operators typically collect the green liquor and transport the green liquor to a causticizing plant to react the sodium carbonate ($Na_2CO_3$) with lime (CaO) to convert the sodium carbonate ($Na_2CO_3$) into sodium hydroxide (NaOH) and thereby reproduce the white liquor.

As the smelt contacts the green liquor in a dissolving tank, the smelt explodes and emits a series of audible sounds. This is generally known as "banging" by those in the industry. The smelt flowing from the spout is typically between 750 degrees Celsius (° C.) to 820° C., while the average temperature of the green liquor is about 70° C. to 100° C. Without being bound by theory, it is believed that the large temperature difference may increase the reactivity of the smelt and green liquor and thereby cause or contribute to banging. If left unregulated, a sudden influx of smelt may cause an explosion in the dissolving tank and recovery boiler, which poses grave safety risks to nearby operating personnel.

To manage smelt dissolution and to avoid excessive noise and the possibility of catastrophic explosions, conventional dissolving tanks generally disrupt the smelt as the smelt falls from the spout. Disruptors may be one or more shatter jets. A shatter jet blasts the falling smelt with steam or other shattering fluid at high pressure to create smelt droplets. These droplets collectively have a greater surface area than an undisrupted smelt flow. The individual droplets also have a smaller volume than an overall undisrupted smelt flow. The increased surface area and smaller amounts of reactants allows for banging explosions that are generally less intense than the explosions would be if the smelt contacted the green liquor as a continuous, uninterrupted, undisrupted flow. Typically, the end of the spout is elevated above the liquid level of green liquor and the shatter jets disrupt falling smelt as the smelt falls from the spout end. The shatter jet nozzles typically cannot be adjusted remotely. When a smelt upset occurs, operators generally cannot safely adjust the discharge rate of disrupting fluid into the dissolving tank.

Occasionally, smelt may cool prematurely in the recovery boiler or spout and decrease or eliminate the smelt flow rate. In this antediluvian state, liquid smelt tends to accumulate behind the obstruction. If the obstruction dislodges, the sudden smelt influx may overwhelm the shatter jet's ability to disrupt the smelt into sufficiently small droplets and an agitator's ability to mix the influx into the green liquor effectively. Moreover, if the deluge is particularly substantial, the smelt may flow over the sides of the spout and bypass the shatter jets entirely. In other scenarios, a shatter jet or agitator may fail. In these situations, the increased volume of smelt contacting the green liquor drastically increases the banging's explosive intensity and explosion risk.

In many mills, operators commonly move in and amongst the processing equipment to monitor process conditions and output. An explosion in the dissolving tank or recovery boiler poses a serious safety risk to personnel in the immediate vicinity, and the resulting fire poses a serious risk to personnel in the rest of the mill. Such explosions also cause an unregulated amount of pollutants to enter the air and groundwater and predicate significant production loss. Explosions of this scale can inactivate a mill for weeks to months.

Previous attempts to address this problem can be seen in the apparatus and method described in U.S. Pat. No. 9,206,548, entitled, "Cooled Smelt Restrictor at Cooled Smelt Spout for Disrupting Smelt Flow from the Boiler," the entirely of which is incorporated here by reference. This apparatus comprises a door that is configured to partially or substantially restrict smelt flow in a closed position. However, this device is a single-use solution that relies on precise timing to prevent an explosion. Because it is a single-use device, operators must shut down the recovery boiler and shut down or re-direct ancillary processes to replace a used "smelt restrictor." The recovery boiler shutdown interrupts production, often for days or weeks.

U.S. Pat. No. 10,012,616, entitled, "Acoustic Emission System and Method for Predicting Explosions in a Dissolving Tank," and incorporated herein by reference, describes a system configured to measure and evaluate banging in order to predict smelt explosions. While these systems have been generally effective at reducing explosions, both systems are reactive and generally trigger a failsafe just moments before an explosion might otherwise occur. Therefore, a failure of one of these systems at a critical moment could result in the same explosions that plagued conventional recovery boilers and dissolving tanks.

Furthermore, undissolved smelt may accumulate at the dissolving tank's floor, which can reduce the quality of the green liquor and increase scaling inside the dissolving tank. Scaling on the primary agitator's propeller increases the mass of the propeller, thereby requiring the motor to expend additional energy to maintain a desired rotational velocity and in extreme cases, reduce the mixing in the dissolving tank increasing the potential for an explosion. Neither of the devices disclosed in U.S. Pat. Nos. 9,206,548 or 10,012,616 address this issue.

SUMMARY OF THE INVENTION

The problem of runaway smelt explosions due to heavy smelt flows in a dissolving tank and the problem of scaling of the primary agitator in the dissolving tank is mitigated by a system comprising an ultrasonic transducer having a transducing end disposed in the dissolving tank, wherein the ultrasonic transducer emits ultrasonic waves above 20 kilohertz ("KHz").

Without being bound by theory, it is contemplated that the ultrasonic waves may destabilize a protective layer of vapor that can form around a smelt droplet in a dissolving tank. A collapsed vapor layer may accelerate the molten smelt droplet's contact with the green liquor, thereby accelerating the rate of the smelt's banging and decelerating the smelt's rate of dissolving into the green liquor for a given set of process conditions. Without ultrasonic waves, it is contemplated that the protective layer of vapor may form a barrier between the molten smelt droplet and the green liquor, thereby permitting the potential accumulation or amalgamation of smelt droplets in the dissolving tank to explosive levels. Such an amalgamation would effectively undermine the disruptor's intended function.

It is further contemplated that the ultrasonic waves may create an energetic environment that prevents pirssonite ($Na_2CO_3 \cdot CaCO_3 \cdot 2H_2O$), calcite ($CaCO_3$), and other precipitates from accumulating on the agitators. Accordingly, another exemplary embodiment may comprise placing an ultrasonic transducer in a green liquor or white liquor conduit or a white liquor holding tank to mitigate scaling.

In certain exemplary embodiments, sensors may be disposed in or around the dissolving tank to monitor the rate of smelt flow into the dissolving tank. These sensors may transduce signals from the dissolving tank and transmit said signals to a data processor such as a computer, a programmable logic controller ("PLC"), a field programmable gate array ("FPGA"), an application-specific integrated circuit ("ASIC"), or other processor. The data processor may modulate the intensity of the ultrasonic waves emitted by the ultrasonic transducer to accommodate changes in smelt flow. In other exemplary embodiments, the data processor may adjust the power or frequency of the ultrasonic transducer in response to changes in process conditions. For example, when the sensors detect an upset condition, the data processor may increase the intensity or the frequency of the ultrasonic waves emitted toward the falling smelt. In certain exemplary embodiments, the data processor may regulate both the intensity and the frequency of the ultrasonic waves.

In still other exemplary embodiments, the data processor may adjust the rate of agitation based upon inputs from the sensors and ultrasonic transducer. In still other exemplary embodiments, the data processor may adjust a discharge rate of the disruptor in response to input from the sensors and ultrasonic transducer. By way of example, the sensors and control system may include the sensors and control system described in U.S. Pat. No. 10,012,616, the entirety of which is incorporated herein by reference.

In other exemplary embodiments, the sensors may include but are not limited to accelerometers, strain sensors, acoustic sensors, temperature sensors, density analyzers (including for example Baumé hydrometers), and density chemical analyzers such as total titratable alkali ("TTA") analyzers, cameras, and combinations thereof.

In an exemplary embodiment, an ultrasonic transducer may be used in conjunction with a disruptor such as a shatter jet nozzle. In such an embodiment, it is believed that the use of an ultrasonic transducer in conjunction with a shatter jet may reduce or eliminate the amount of disrupting fluid (e.g. steam) used to disrupt the smelt into smelt droplets. Furthermore, it is contemplated that that the use of the ultrasonic transducer system described herein can agitate the dissolving liquid and facilitate the circulation and dissolution of smelt droplets in the dissolving liquid (e.g. green liquor). As a result, a primary agitator (e.g. a main dissolving tank or "MDT" agitator) may be operated to use less energy to circulate the dissolving liquid in the dissolving tank.

The exemplary systems described herein may further increase personnel safety by eliminating the need for operating personnel to adjust manually the flow of fluid through the shatter jets during normal, upset, or transient conditions.

BRIEF DESCRIPTION OF THE DRAWINGS

The foregoing will be apparent from the following more particular description of exemplary embodiments of the disclosure, as illustrated in the accompanying drawings in which like reference characters refer to the same parts throughout the different views. The drawings are not necessarily to scale, with emphasis instead being placed upon illustrating the disclosed embodiments.

DETAILED DESCRIPTION OF THE INVENTION

Figure 1:
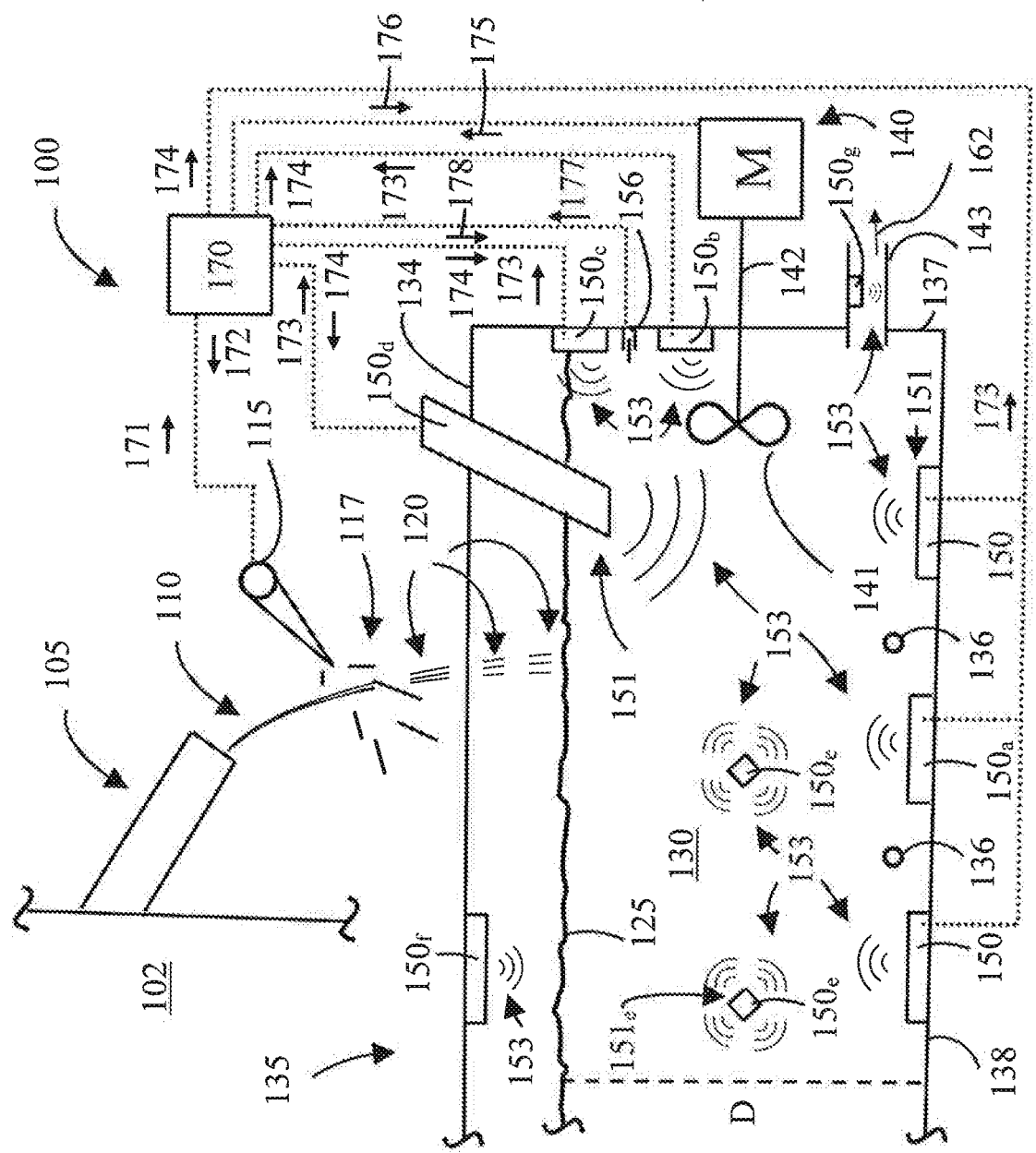
FIG. 1 is a schematic side view of an exemplary ultrasonic smelt dissolving and shattering system.

The following detailed description of the preferred embodiments is presented only for illustrative and descriptive purposes and is not intended to be exhaustive or to limit the scope and spirit of the invention. The embodiments were selected and described to best explain the principles of the invention and its practical application. One of ordinary skill in the art will recognize that many variations can be made to the invention disclosed in this specification without departing from the scope and spirit of the invention.

Corresponding reference characters indicate corresponding parts throughout the several views. Although the drawings represent embodiments of various features and components according to the present disclosure, the drawings are not necessarily to scale and certain features may be exaggerated in order to better illustrate embodiments of the present disclosure, and such exemplifications are not to be construed as limiting the scope of the present disclosure in any manner.

References in the specification to "one embodiment," "an embodiment," "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Although specific terms are used in the following description for the sake of clarity, these terms are intended to refer only to the particular structure of the embodiment selected for illustration in the drawings, and are not intended to define or limit the scope of the disclosure.

The singular forms "a," "an," and "the" include plural referents unless the context clearly dictates otherwise. Numerical values should be understood to include numerical values which are the same when reduced to the same number of significant figures and numerical values which differ from the states value by less than the experimental error of conventional measurement technique of the type described in the present application to determine the value.

All ranges disclosed herein are inclusive of the recited endpoint and are independently combinable (for example, the range "from 2 millimeters to 10 millimeters" is inclusive of the endpoints, 2 millimeters and 10 millimeters, and all intermediate values).

As used herein, approximating language may be applied to modify any quantitative representation that may vary without resulting in a change in the basic function to which it is related. Accordingly, a value modified by a term or terms, such as "about" and "substantially," may not be limited to the precise values specified. The modifier "about" should also be considered as disclosing the range defined by the absolute values of the two endpoints. For example, the expression "from about 2 to about 4" also discloses the range "from 2 to 4."

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet' and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow of fluids through an upstream component prior to flowing through the downstream component.

The terms "horizontal" and "vertical" are used to indicate direction relative to an absolute reference, i.e. ground level. However, these terms should not be construed to require structure to be absolutely parallel or absolutely perpendicular to each other. For example, a first vertical structure and a second vertical structure are not necessarily parallel to each other. The terms "top" and "floor" or "base" are used to refer to locations/surfaces where the top is always higher than the floor/base relative to an absolute reference, i.e. the surface of the Earth. The terms "upwards" and "downwards" are also relative to an absolute reference; an upwards flow is always against the gravity of the Earth.

The term "directly," wherein used to refer to two system components, such as valves or pumps, or other control devices, or sensors (e.g. temperature or pressure), may be located in the path between the two named components.

FIG. 1 is a schematic representation of an exemplary ultrasonic smelt dissolving and shattering system 100. FIG. 1 depicts a recovery boiler 102 having a spout 105 adjacent to a dissolving tank 135. The spout 105 directs a volume of smelt 110 into the dissolving tank 135. As seen in the cutaway, the dissolving tank 135 contains a dissolving liquid 130. The dissolving liquid 130 is commonly green liquor. The liquid level 125 of the dissolving liquid 130 is generally below the top 134 of the dissolving tank 135. A primary agitator 140 driven by a motor M agitates the dissolving liquid 130 and helps equalize the dissolving liquid's temperature. The motor M may be a variable speed drive motor. Although the primary agitator 140 depicted in FIG. 1 is a propeller 141 connected to a driveshaft 142, it will be understood by those having ordinary skill in the art that an "agitator" is a device configured to move dissolving liquid 130 through the dissolving tank 135. Other agitators may include for example, fluid jets 136, devices that undulate the dissolving liquid 130, and other rotating bodies.

Primary agitators 140 typically comprise a propeller 141 or other mechanical implement extending into the dissolving liquid 130. Secondary agitators (see 136) may be fluid jets 136 that inject air or other fluid into the dissolving liquid 130 to agitate the dissolving liquid 130. While it is possible to use secondary agitators (see 136) simultaneously with primary agitators 140, operators more commonly activate secondary agitators (see 136) when primary agitators 140 fail or underperform. As the volume of smelt 110 falls from the spout 105, a disruptor 115, for example, a "shatter jet," directs a pressurized disrupting fluid 117 (commonly in the form of steam) toward the falling smelt 110. The disrupting fluid 117 interrupts the continuous smelt stream 110 and thereby creates smelt droplets 120. While shatter jets are common types of disruptors 115, it will be understood that other devices that break up or dropletize the smelt stream 110 falling form the spout 105 is a "disruptor" 115.

After the smelt droplets 120 contact the dissolving liquid 130, the smelt droplets 120 emit an audible bang and eventually dissolve into the dissolving liquid 130. In an upset condition, the amount of undissolved smelt in the dissolving tank 135 increases. When the amount of undissolved smelt increases in the dissolving tank 135 due to an increased flow rate, the incoming smelt stream 110 can overwhelm a disruptor's ability to shatter the smelt stream 110 into sufficiently small smelt droplets 120. Without being bound by theory, it is believed that the vast differences in temperatures between the volume of smelt 110 and the dissolving liquid 130 causes the smelt droplets 120 to explode soon after contacting the dissolving liquid 130.

It was believed that an increased rate of smelt flow into the dissolving tank 135 was the only cause of upset conditions. However, Applicant discovered that a layer of vapor 245 (FIG. 2) forms around the smelt droplet 220 (FIG. 2) when the smelt droplet 220 has a temperature in the range of about 750° C. to about 820° C. and the dissolving liquid 230 (FIG. 2) has a temperature in the range of about 70° C. to about 100° C. This vapor layer 245 may insulate the smelt droplet 220 from the dissolving liquid 130 and thereby allow the smelt droplets 120, 220 to accumulate and remain undissolved in the dissolving tank 135 even at nominal smelt flow rates.

To mitigate this problem, Applicant developed a system comprising an ultrasonic transducer 150 disposed within the dissolving tank 135. The ultrasonic transducer 150 has a transducer end 151 that directs ultrasonic waves 153 having a frequency above 20 KHz into the dissolving liquid 130. The ultrasonic transducer 150 may be, by way of example, a piezoelectric transducer or a magnetostrictive transducer. If the ultrasonic transducer 150 is a piezoelectric transducer, the piezoelectric crystal may be barium titanate, lead zirconate titanate ("PZT"), or other piezoelectric crystal.

In operation, a piezoelectric ultrasonic transducer 150 vibrates rapidly in concert with an electrical signal oscillating an ultrasonic frequency. The electrical signal may originate from a power supply or other power source. The resulting movement of the ultrasonic transducer creates a series of compression waves (see 153) that create millions of microscopic voids in the dissolving liquid 130. These "voids" or "cavitation bubbles" collapse and release significant energy. For example, a collapsing cavitation bubble may reach temperatures above 4,726.85° C. and pressures above 135 megapascals ("MPa"). For comparison, the surface of the sun averages about 5,504.85° C. Magnetostrictive ultrasonic transducers 150 operate similarly to the piezoelectric ultrasonic transducer 150 except that a magnetic field is used to vibrate the megnetostrictive transducer instead of an electrical signal.

Without being bound by theory, it is believed that the ultrasonic waves 153 and resulting cavitation may cause the vapor layer 245 to collapse faster than in dissolving tanks 135 lacking such an ultrasonic transducer 150. The ultrasonic transducer 150 therefore reduces the delay of the smelt droplets 120 dissolving in the dissolving liquid 130.

FIG. 1 depicts several exemplary placements of ultrasonic transducers 150 disposed in a dissolving tank 135. It will be understood that different exemplary embodiments may have a subset of the depicted ultrasonic transducer 150 placements (e.g. ultrasonic transducers $150_a$ disposed at the dissolving tank floor 138) or a combination of subsets (e.g. ultrasonic transducers $150_a$ disposed at the dissolving tank's floor 138 and ultrasonic transducers $150_b$, $150_c$ disposed at a side 137 of the dissolving tank 135). Furthermore, in other exemplary embodiments, one or more ultrasonic transducers 150 can be engaged to the dissolving tank 135, for example, being engaged to the side 137 of the dissolving tank 135, being engaged to the top 134 of the dissolving tank 135, or being engaged to the floor 138 of the dissolving tank 135.

FIG. 1 shows multiple ultrasonic transducers $150_a$ disposed at the dissolving tank's floor 138. The depicted embodiment further illustrates an ultrasonic transducer $150_b$ disposed on the side 137 of the dissolving tank 135 under the liquid level 125. A further ultrasonic transducer $150_c$ is placed on the side 137 of the dissolving tank 135 at the liquid level 125. FIG. 1 also depicts an ultrasonic transducer $150_d$ extending from the top 134 of the dissolving tank 135 down into the dissolving liquid 130. Ultrasonic transducer $150_f$ also extends from the top 134 of the dissolving tank 135, but does not extend into the dissolving liquid 130. Ultrasonic transducers $150_e$ have transducer ends $151_e$ disposed in the dissolving liquid 130 substantially away from the floor 138, top 134, and sides 137 of the dissolving tank 135. A conduit ultrasonic transducer $150_g$ is disposed in an outlet conduit 143 fluidly communicating with the dissolving tank 135. Exiting green liquor 162 flows downstream to the next recausticizing step, which is usually a green liquor clarifier configured to allow particles to settle out of the green liquor over several hours.

Placement of the ultrasonic transducers 150 may vary among exemplary embodiments depending in part upon the expected ultrasonic wave intensity and expected propagation. Propagation depends in part upon the power consumed by the ultrasonic transducer 150. Wave propagation is also a function of the dissolving liquid's density and the distance and the medium through which the ultrasonic wave 153 travels.

For example, selecting an ultrasonic transducer 150 that has the power to transmit ultrasonic waves 153 though the depth D of the dissolving liquid 130 and placing the ultrasonic transducers $150_a$ at the dissolving tank's floor 138 may be preferable to placing a similarly configured ultrasonic transducer $150_b$ on the side 137 of the dissolving tank 135. Ultrasonic waves 153 from a vertically disposed ultrasonic transducer $150_b$ on a side 137 of the dissolving tank 135 may reflect off the opposing sidewall and interfere with oncoming ultrasonic waves 153.

Figure 2:
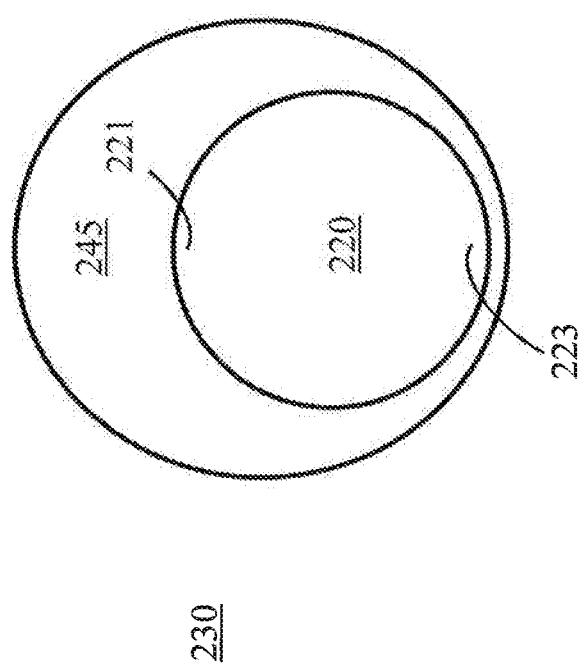
FIG. 2 is a schematic representation of a smelt droplet enveloped in an insulating vapor layer.

The insulating vapor layer 245 is asymmetrically disposed around each smelt droplet 220. As FIG. 2 depicts, buoyancy causes a majority of the vapor layer 245 to be disposed above the downward falling smelt droplet 220. The top 221 of the smelt droplet 220 is generally hotter than the bottom 223 of the smelt droplet 220 and this temperature differential further contributes to the vapor layer's asymmetric distribution. Ultrasonic waves 153 coming from the dissolving tanks' floor 138 may therefore interact with the thinner portion of the vapor layer 245 thereby facilitating the vapor layer's collapse.

To reduce the power needed to transmit ultrasonic waves 153 from the floor 138 of the dissolving tank 135 to the liquid level 125, it can be desirable to place the transducer end $151_e$ of an ultrasonic transducer $150_e$ under the smelt droplets 120 but substantially above the dissolving tank's floor 138. "Substantially above" the dissolving tank's floor 138 may be about halfway from the liquid level 125, less than one third the depth D from the liquid level 125, or other distance sufficient to allow the ultrasonic waves 153 to travel from the transducer end $151_e$ upward to the liquid level 125 while maintaining a frequency above 20 KHz. In other exemplary embodiments, an ultrasonic transducer 150 can be disposed at the midpoint of the depth D of the dissolving liquid 130 in the dissolving tank 135. An ultrasonic transducer 150 disposed closer to the bottoms 223 of the smelt droplets 220 than the dissolving tank floor 138 will reduce the distance the ultrasonic wave 153 will travel and therefore the power needed to generate the ultrasonic wave 153.

By reducing the delay between smelt droplet 120 contact with the dissolving liquid 130 and the dissolving of the smelt droplets 120 under nominal operating conditions, it is contemplated that mill operators may be able to reduce the amount of disrupting fluid 117 needed to dropletize the smelt stream 110. The reduced disrupting fluid 117 may result in energy savings while improving safety. For this reason, it is contemplated that a disruptor 115 may be omitted in certain exemplary embodiments.

The ultrasonic waves 153 may further create an energetic environment in the dissolving tank 135 that vibrates the primary agitators 140, sides 137, and other metal components in the dissolving tank 135. Without being bound by theory, the vibration of these metal components may prevent pirssonite ($Na_2CO_3 \cdot CaCO_3 \cdot 2H_2O$), calcite ($CaCO_3$), and other precipitates from accumulating on the primary agitators 140, sides 137, and other metal components in the dissolving tank 135 and in the outlet conduit 143. To delay scaling in the past, operators increased the rate of speed of the primary agitators 140. With the adoption of an exemplary system described herein, it is contemplated that operators may be able to reduce the speed of the primary agitators 140, thereby saving energy and cleaning costs while increasing reliability and mixing efficiency.

Sensors 156 may be disposed in or around the dissolving tank 135 to monitor smelt flow conditions. The sensors 156 or the data processor 170 may be configured to adjust the intensity of the ultrasonic waves 153 based on the rate of smelt flow into the dissolving tank 135 or based on other process conditions. Other "process conditions" may include, for example, temperature, acoustic emissions from the banging, and the density of the dissolving liquid 130.

Sensors 156 used in an exemplary ultrasonic smelt dissolving and shattering system 100 may be selected from the group consisting of accelerometers, strain sensors, acoustic sensors, temperature sensors, cameras, and density analyzers (including, for example, Baumé hydrometers, or TTA analyzers), or combinations thereof. The ultrasonic smelt dissolving and shattering system 100 may comprise a data processor 170 configured to evaluate process conditions and to adjust a wave condition of the ultrasonic transducer 150 based upon the process conditions. In certain exemplary embodiments, the wave condition may be a wave frequency. In other exemplary embodiments, the wave condition may be a wave intensity. In still other exemplary embodiments, the wave condition may be both a wave frequency and a wave intensity (i.e. power transferred per unit area).

In certain exemplary embodiments, the data processor may be selected from the group consisting of a computer, a programmable logic controller ("PLC"), a field programmable gate array ("FPGA"), an application-specific integrated circuit ("ASIC"), or other processor.

In the depicted exemplary embodiment, the data processor 170 is in signal communication with the ultrasonic transducers 150, the sensors 156, the disruptor 115, and the primary agitator 140. Signal communication may be achieved through wires or wirelessly. It is further contemplated that "signal communication" may comprise the use of one or more intermediate signal processors (e.g. amplifiers, analog to digital converters, relays, filters, etc.) configured to modify and/or transmit the signals between the data processor 170 and the ultrasonic transducers 150, the sensors 156, the disruptor 115, and the primary agitator 140. It will be understood that other exemplary ultrasonic smelt dissolving and shattering systems 100 may not have a data processor 170 in signal communication with each of the ultrasonic transducers 150, the sensors 156, the disruptor 115, and the primary agitator 140.

Although not depicted, it is contemplated that the ultrasonic transducer $150_f$ extending from the top 134 of the dissolving tank 135, the ultrasonic transducers $150_e$ suspended in the dissolving liquid 130, and the conduit ultrasonic transducer $150_g$ can be in signal communication with the data processor 170 in a way substantially similar to the other depicted ultrasonic transducers $150_a$, $150_b$, $150_c$, $150_d$. In other exemplary embodiments, the secondary agitator (see 136) may be in signal communication with the data processor 170. Combinations of any of the disclosed embodiments are within the scope of this disclosure.

Because it is contemplated that the use of ultrasonic transducers 150 may allow operators to reduce the disruption rate and the agitation rate, it is further contemplated that the data processor 170 can be configured to adjust the rate of disruption and/or agitation based upon the signal output from the sensors 156 and ultrasonic transducers 150. As an example of an exemplary method, the data processor 170 may receive a transducer output signal 173 from an ultrasonic transducer 150 and a sensor output signal 177 from a sensor 156. The transducer output signal 173 may indicate that the ultrasonic transducers 150 are emitting ultrasonic waves 153 at maximum power. The sensor output signal 177 may indicate that the density of the dissolving liquid 130 is above the desirable range. The data processor 170 may analyze the signals 173, 177 and send an agitator input signal 176 to the agitator (see 140, 136) to increase the rate of agitation. A desirable or "nominal" range for the density of the dissolving liquid 130 is typically between 1,100 kilograms per meter cubed ("$kg/m^3$") and 1,180 $kg/m^3$. If the sensor 156 is a temperature sensor, the desirable or "nominal" temperature range for the dissolving liquid 130 if the dissolving liquid 130 is green liquor is about 70° C. to 100° C.

By way of another example, the data processor 170 may receive a transducer output signal 173 indicating that the ultrasonic transducers 150 are emitting, ultrasonic waves 153 at maximum power. The sensor output signal 177 may indicate that the temperature of the dissolving liquid 130 is above the desirable range. An agitator output signal 175 may indicate that the agitator (see 140, 136) is outputting at maximum capacity. If the agitator is a primary agitator 140, the agitator 140 could be rotating at maximum capacity. If the agitator is a secondary agitator (see 136), the secondary agitator (see 136) outputting at maximum capacity could be a fluid jet 136 injecting fluid into the dissolving tank 135 at a maximum rate. The data processor 170 can analyze the signals 173, 175, 177 and send a disruptor input signal 172 to the disruptor 115 to increase the rate of disrupting fluid 117 output, thereby increasing the disruption rate.

In other exemplary embodiments, the data processor 170 may send a transducer input signal 174 to the transducers to adjust the power output of the transducers, change a physical property of the ultrasonic waves 153 or otherwise adjust the ultrasonic transducers' emissions. In still other exemplary embodiments, the data processor 170 may receive a disruptor output signal 171 indicating the amount of disrupting fluid 117 the disruptor 115 emits per unit of time.

The data processor 170 may be further configured to adjust a discharge rate at which disrupting fluid 117 exits the disruptor 115 based on the process condition by sending a disruptor input signal 172 to the disruptor 115. In still other exemplary embodiments, the data processor 170 is further configured to adjust the power of the agitator (see 140, 136) based on a process condition by sending an agitator input signal 176 to the agitator (see 140, 136) and thereby adjust an agitation rate.

In certain exemplary embodiments, a method for monitoring and adjusting a rate of smelt dissolving in a dissolving tank 135 comprises: receiving a sensor output signal 177 from an sensor 156, the sensor output signal 177 indicating a process condition at a measured time, receiving a transducer output signal 173 from an ultrasonic transducer 150, receiving an agitator output signal 175 from an agitator (see 140, 136), receiving a disruptor output signal 171 from a disruptor 115, and comparing the sensor output signal 177, transducer output signal 173, agitator output signal 175, and disruptor output signal 171 to preprogrammed acceptable operating conditions to determine whether the smelt 110 is dissolving at an acceptable rate.

An exemplary method further comprises sending a transducer input signal 174 to the transducer 150 to adjust the power output of the transducer 150, intensity, or frequency of the ultrasonic wave 153. An exemplary method may further comprise sending an agitator input signal 176 to the agitator (see 140, 136) to adjust the rate of agitation to return the dissolving tank 135 to desirable dissolving conditions. An exemplary method may further comprise sending a disruptor input signal 172 to the disruptor 115 to adjust the volume of disrupting fluid 117 exiting the disruptor 115 to return the dissolving tank 135 to desirable dissolving conditions. Yet another exemplary method may further comprise sending a sensor input signal 178 to the sensor 156 to adjust the sensitivity of the sensor 156.

Another exemplary method for monitoring and adjusting a rate of smelt dissolving in a dissolving tank 135 comprises: receiving a sensor output signal 177 from a sensor 156 disposed within a dissolving tank 135, the sensor output signal 177 indicating a process condition at a measured time, receiving a transducer output signal 173 from an ultrasonic transducer 150 disposed in a dissolving tank 135 indicating a transducer output (see 153), comparing the sensor output signal 177 with a programmed desirable operation range for the process condition, comparing the transducer output signal 173 with a programmed desirable operation range for the transducer, sending a transducer input signal 174 to the transducer 150 to adjust the transducer output (see 153) when the sensor output signal 177 is outside the desirable operation range for the process condition.

An exemplary method may further comprise: receiving an agitator output signal 175 from a primary agitator 140 indicating a rate of agitation, and sending an agitator input signal 176 to the agitator (see 140, 136) to adjust the rate of agitation when the transducer output. (see 153) is outside of the programmed desirable operation range for the transducer 150.

Another exemplary method may further comprise: receiving a disruptor output signal 171 from a disruptor 115 indicating a rate of disruption, and sending a disruptor input signal 172 to the disruptor 115 to adjust the rate of disruption when the transducer output (see 153) is outside of the programmed desirable operation range for the transducer 150. A further exemplary method may comprise pulsing the ultrasonic transducers 150 between an on and an off position over a period to increase smelt dissolving and prevention of scaling. Pulsing may further comprise alternating between a first transducer output and a second transducer output wherein the first transducer output and the second transducer output comprise different power levels, wave intensity, wave frequency, or other wave condition.

Yet a further exemplary method may further comprise: receiving a conduit transducer output signal (see 173) from a conduit ultrasonic transducer $150_g$ disposed in an outlet conduit 143 indicating a conduit transducer output, comparing the conduit transducer output signal (see 173) with a programmed desirable operation range for the conduit ultrasonic transducer $150_g$, sending a conduit transducer input signal (see 174) to the conduit ultrasonic transducer $150_g$ to adjust the conduit transducer output when the sensor output signal 177 is outside the desirable operation range for the process condition.

An exemplary system 100 comprises: a dissolving tank 135, a spout 105 adjacent to the dissolving tank 135, wherein the spout 105 is configured to convey a volume of smelt 110 into the dissolving tank 135, an agitator (see 140, 136) disposed in the dissolving tank 135, wherein the agitator (see 140, 136) is configured to mix the volume of smelt 110 into a dissolving liquid 130 in the dissolving tank 135, and an ultrasonic transducer 150, wherein the ultrasonic transducer 150 is configured to emit ultrasonic waves 153 within the dissolving tank 135 at a frequency above 20 kilohertz.

An exemplary ultrasonic smelt dissolving and shattering system 100 comprises: a dissolving tank 135, a spout 105 adjacently disposed to the dissolving tank 135, wherein the spout 105 is configured to direct a volume of smelt 110 into the dissolving tank 135, an agitator (see 140, 136) disposed at a side 137 of the dissolving tank 135, an ultrasonic transducer 150, having a transducer end 151 configured to emit ultrasonic waves 153 above 20 kilohertz in the dissolving tank 135, a sensor 156 disposed proximate to the dissolving tank 135, wherein the sensor 156 is configured to measure a process condition within the dissolving tank 135, a data processor 170 configured to receive a sensor output signal 177 from the sensor 156, wherein the sensor output signal 177 indicates the process condition at a measured time, wherein the data processor 170 is further configured to compare the sensor output signal 177 to a programmed desirable operation range for the process condition, and to send a transducer input signal 174 to the ultrasonic transducer 150 to adjust a transducer output if the sensor output signal 177 is outside of the programmed desirable operation range.

While this invention has been particularly shown and described with references to exemplary embodiments thereof, it will be understood by those skilled in the art that various changes in form and details may be made therein without departing from the scope of the invention encompassed by the appended claims.

What is claimed is:

1. A ultrasonic smelt dissolving and shattering system comprising:
    a dissolving tank;
    a spout adjacently disposed to the dissolving tank, wherein the spout is configured to direct a volume of smelt into the dissolving tank;
    an agitator disposed at a side of the dissolving tank;
    an ultrasonic transducer, having a transducer end configured to emit ultrasonic waves above 20 kilohertz in the dissolving tank;
    a sensor disposed proximately to the dissolving tank, wherein the sensor is configured to measure a process condition within the dissolving tank;
    a data processor configured to receive a sensor output signal from the sensor, wherein the sensor output signal indicates the process condition at a measured time, wherein the data processor is further configured to compare the sensor output signal to a programmed operation range for the process condition, and to send a transducer input signal to the ultrasonic transducer to adjust a transducer output if the sensor output signal is outside of the programmed operation range.

2. The system of claim 1, wherein the data processor is further configured to receive a transducer output signal indicating the transducer output, wherein the data processor is further configured to send an agitator input signal to the agitator to adjust the rate of agitation when the transducer output signal indicates that the transducer output is at a maximum and when the sensor output signal indicates that the process condition is outside of the programmed range.

3. The system of claim 1 further comprising a disruptor configured to disrupt the volume of smelt flowing from the spout into the dissolving tank to thereby form smelt droplets, wherein a disrupting fluid exits the disruptor at a disruptor discharge rate.

4. The system of claim 3, wherein the data processor is further configured to receive a transducer output signal indicating the transducer output, wherein the data processor is further configured to send a disruptor input signal to the disruptor to adjust the rate of disruption when the transducer output signal indicates that the transducer output is at a maximum and when the sensor output signal indicates that the process condition is outside of the programmed range.

5. The system of claim 1, wherein the sensor is selected from the group consisting of: an accelerometer, a strain sensor, an acoustic sensor, a temperature sensor, a density analyzer, a Baumé hydrometer, a total titratable alkali analyzer, a camera, and combinations thereof.

6. The system of claim 1 further comprising multiple sensors disposed in the dissolving tank, wherein the multiple sensors are configured to measure multiple process conditions.

7. The system of claim 1 further comprising multiple ultrasonic transducers disposed in the dissolving tank, wherein each ultrasonic transducer has a transducer end configured to emit ultrasonic waves at a frequency above 20 KHz.

8. The system of claim 1 further comprising an outlet conduit fluidly communicating with the dissolving tank, wherein a conduit ultrasonic transducer is disposed in the conduit, and wherein the conduit ultrasonic transducer is configured to emit ultrasonic waves at a frequency above 20 KHz.

9. A method for monitoring and adjusting a rate of smelt dissolving in a dissolving tank comprising:
receiving a sensor output signal from a sensor disposed within the dissolving tank, the sensor output signal indicating a process condition at a measured time;
receiving a transducer output signal from an ultrasonic transducer disposed in the dissolving tank indicating a transducer output;
comparing the sensor output signal with a programmed operation range for the process condition;
comparing the transducer output signal with a programmed operation range for the transducer;
sending a transducer input signal to the transducer to adjust the transducer output when the sensor output signal is outside the operation range for the process condition.

10. The method of claim 9 further comprising receiving an agitator output signal from an agitator indicating a rate of agitation, and sending an agitator input signal to the agitator to adjust the rate of agitation when the transducer output is outside of the programmed operation range for the transducer.

11. The method of claim 9 further comprising receiving a disruptor output signal from a disruptor indicating a rate of disruption, and sending a disruptor input signal to the disruptor to adjust the rate of disruption when the transducer output is outside of the programmed operation range for the transducer.

12. The method of claim 9 further comprising sending a sensor input signal to the sensor to adjust a sensitivity to the process condition.

13. The method of claim 9 further comprising pulsing the ultrasonic transducer, wherein pulsing the ultrasonic transducer comprises alternating between a first transducer output and a second transducer output wherein the first transducer output and the second transducer output comprise different power levels, wave intensity, wave frequency, or other wave condition.

14. The method of claim 9 further comprising: receiving a conduit transducer output signal from a conduit ultrasonic transducer disposed in an outlet conduit indicating a conduit transducer output, comparing the conduit transducer output signal with a programmed operation range for the conduit ultrasonic transducer, sending a conduit transducer input signal to the conduit ultrasonic transducer to adjust the conduit transducer output when the sensor output signal is outside the operation range for the process condition.

* * * * *

UNITED STATES PATENT AND TRADEMARK OFFICE
CERTIFICATE OF CORRECTION

PATENT NO. : 10,557,235 B2  
APPLICATION NO. : 16/040333  
DATED : February 11, 2020  
INVENTOR(S) : Mark LeBel Page 1 of 1

It is certified that error appears in the above-identified patent and that said Letters Patent is hereby corrected as shown below:

On the Title Page

Please delete the title (54) and in the Specification, Column 1, Lines 1-2:
"ULTRASONIC SEMELT DISSOLVING AND SHATTERING SYSTEM"

And insert:
--ULTRASONIC SMELT DISSOLVING AND SHATTERING SYSTEM--

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*